(12) United States Patent
Ji et al.

(10) Patent No.: US 12,128,248 B2
(45) Date of Patent: Oct. 29, 2024

(54) OPTICAL PROBE

(71) Applicant: Ewha University-Industry Collaboration Foundation, Seoul (KR)

(72) Inventors: Chang-Hyeon Ji, Seoul (KR); Sang Beom Jun, Seoul (KR)

(73) Assignee: Ewha University—Industry Collaboration Foundation, Seoul (KR)

( * ) Notice: Subject to any disclaimer, the term of this patent is extended or adjusted under 35 U.S.C. 154(b) by 162 days.

(21) Appl. No.: 17/450,127

(22) Filed: Oct. 6, 2021

(65) Prior Publication Data

US 2022/0105360 A1 Apr. 7, 2022

(30) Foreign Application Priority Data

Oct. 7, 2020 (KR) .................. 10-2020-0129157

(51) Int. Cl.
*A61N 5/06* (2006.01)
(52) U.S. Cl.
CPC .......... *A61N 5/0622* (2013.01); *A61N 5/0601* (2013.01); *A61N 2005/063* (2013.01); *A61N 2005/0665* (2013.01)
(58) Field of Classification Search
CPC ................ A61N 5/0622; A61N 5/0601; A61N 2005/063; A61N 2005/0665; A61N 2005/0612; A61B 5/24; A61B 5/6877; A61B 2562/046
See application file for complete search history.

(56) References Cited

U.S. PATENT DOCUMENTS

| | | | |
|---|---|---|---|
| 2009/0002794 A1* | 1/2009 | Weir | A61B 1/07 359/213.1 |
| 2010/0062157 A1* | 3/2010 | Hata | B82Y 40/00 427/249.1 |
| 2011/0295331 A1* | 12/2011 | Wells | A61N 5/0601 607/3 |
| 2012/0287420 A1* | 11/2012 | McLaughlin | |
| 2013/0030274 A1 | 1/2013 | Jamieson et al. | |
| 2013/0046148 A1 | 2/2013 | Tathireddy et al. | |
| 2013/0079615 A1 | 3/2013 | Yoon et al. | |
| 2015/0047179 A1* | 2/2015 | Seymour | A61B 5/24 29/600 |
| 2017/0304625 A1* | 10/2017 | Buschman | |

FOREIGN PATENT DOCUMENTS

KR 101150422 B1 6/2012
KR 20200010879 A 1/2020

* cited by examiner

*Primary Examiner* — Joseph M Dietrich
(74) *Attorney, Agent, or Firm* — Downs Rachlin Martin PLLC (57) ABSTRACT

An optical probe includes a light source configured to generate an optical signal, a plurality of waveguides configured to guide the optical signal to a target, a plurality of electrodes configured to record an electrical signal generated by the target, and a modulator configured to transmit the optical signal of the light source to at least one target waveguide from among the plurality of waveguides.

10 Claims, 8 Drawing Sheets

OPTICAL PROBE

CROSS-REFERENCE TO RELATED APPLICATION

This application claims the benefit of Korean Patent Application No. 10-2020-0129157 filed on Oct. 7, 2020, in the Korean Intellectual Property Office, the entire disclosure of which is incorporated herein by reference for all purposes.

BACKGROUND

1. Field of the Invention

One or more example embodiments relate to an optical probe.

2. Description of the Related Art

An optical probe that uses an optical signal to stimulate or suppress nerve cells and obtains an electrical signal from the stimulated or suppressed nerve cells is being developed. According to related art, to stimulate or suppress the nerve cells included in the brain, the spinal cord, and the like, researchers are using an optogenetics technology to conduct research on behavioral changes of a target subject or to treat a disease. For example, a device that stimulates nerve cells through a neural probe formed with a waveguide and extracts an electrical signal generated by the stimulated nerve cell may be provided. Disclosed in the US Patent Application Publication No. 2013/0030274 is an integrated optical neural probe.

SUMMARY

Example embodiments provide an optical probe that selectively stimulates a plurality of nerve cells in a brain or a spinal cord and extracts an electrical signal generated thereby.

According to an aspect, there is provided an optical probe including a light source configured to generate an optical signal, a plurality of waveguides configured to guide the optical signal to a target, a plurality of electrodes configured to record an electrical signal generated by the target, and a modulator configured to transmit the optical signal of the light source to at least one target waveguide from among the plurality of waveguides.

The modulator may include a mirror that rotates around a first direction intersecting with a longitudinal direction of the plurality of waveguides and reflects the optical signal to the at least one target waveguide.

The mirror may rotate around a second direction intersecting with the longitudinal direction of the plurality of waveguides and the first direction.

The modulator may include an array of mirrors disposed to correspond to the plurality of waveguides. The mirrors may rotate around a direction intersecting with a longitudinal direction of the plurality of waveguides and reflect the optical signal to the at least one target waveguide.

The mirrors may include a first set including at least one mirror reflecting the optical signal in a direction toward the at least one target waveguide, and a second set including remaining mirrors reflecting the optical signal in a direction not toward the plurality of waveguides.

The modulator may include a light condensing element that linearly moves in a first direction intersecting with a longitudinal direction of the plurality of the waveguides or in a second direction intersecting with the longitudinal direction and the first direction for condensing the optical signal to the at least one target waveguide.

The modulator may include a frame having a plurality of openings corresponding to the plurality of waveguides, and a plurality of opening degree control members configured to control an opening degree corresponding to the at least one target waveguide among the plurality of openings.

The plurality of opening degree control members may each include a cantilever arm. The modulator may further include a driving element configured to control a slope of the cantilever arm.

The plurality of opening degree control members may each include an organic compound having an optical anisotropy. The modulator may further include a driving element configured to determine a directionality of the organic compound.

The optical probe may further include a plurality of light condensers connected to the plurality of waveguides for receiving the optical signal from the modulator.

Additional aspects of example embodiments will be set forth in part in the description which follows and, in part, will be apparent from the description, or may be learned by practice of the disclosure.

According to example embodiments, an optical probe may selectively stimulate a plurality of nerve cells in a brain and a spinal cord and extract an electrical signal generated thereby.

Additional aspects of example embodiments are not limited to what is described above, and other aspects that are not described above may also be learned by those skilled in the art from the following description.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, some examples will be described in detail with reference to the accompanying drawings. However, various alterations and modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Although terms of "first," "second," and the like are used to explain various components, the components are not limited to such terms. These terms are used only to distinguish one component from another component. For example, a first component may be referred to as a second component, or similarly, the second component may be referred to as the first component within the scope of the present disclosure. When it is mentioned that one component is "connected" or "accessed" to another component, it may be understood that the one component is directly connected or accessed to another component or that still other component is interposed between the two components. In addition, it should be noted that if it is described in the specification that one component is "directly connected" or "directly joined" to another component, still other component may not be present therebetween. Likewise, expressions, for example, "between" and "immediately between" and "adjacent to" and "immediately adjacent to" may also be construed as described in the foregoing.

Example embodiments will be described in detail with reference to the accompanying drawings. When describing the example embodiments with reference to the accompanying drawings, like reference numerals refer to like components and a repeated description related thereto will be omitted.

Figure 1:
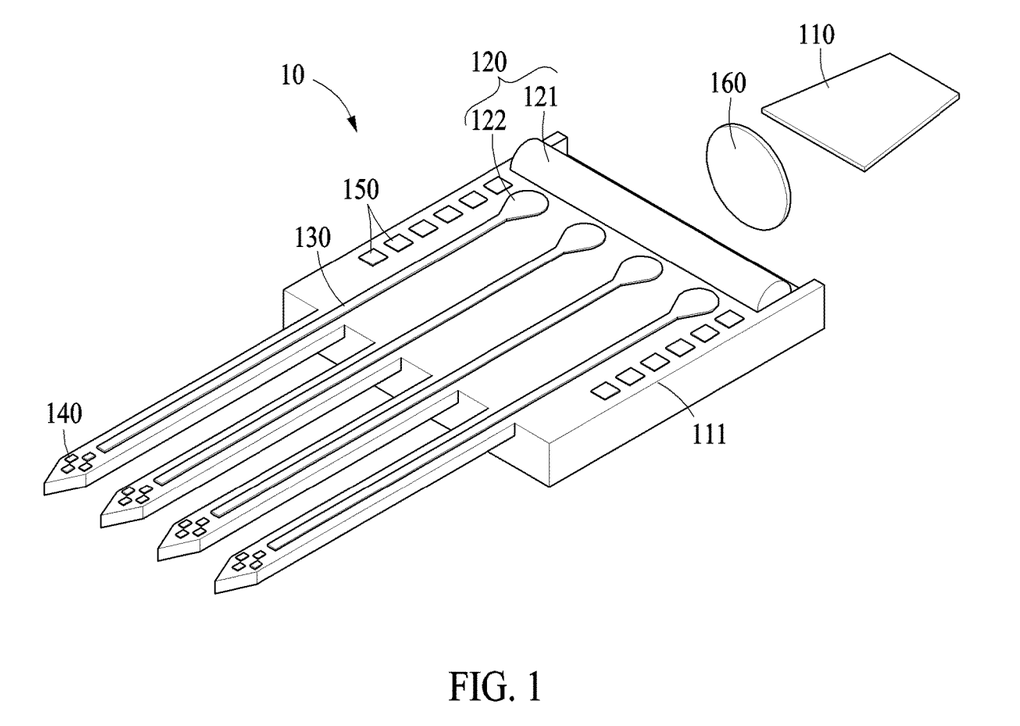
FIG. 1 is a diagram illustrating an optical probe according to an example embodiment.

Referring to FIG. 1, an optical probe 10 may select at least one waveguide 130 from among a plurality of waveguides 130, transmit an optical signal to a target through the at least one selected waveguide 130, and obtain an electrical signal generated by the target. An operation of selecting described herein may be construed as an optical signal being transmitted to a target through at least one target waveguide 130 among the plurality of waveguides 130 and the remaining non-target waveguides 130 not being used. In addition, the term "target" may include nerve cells in a brain, a spinal cord, and the like.

The optical probe 10 may include a power source 110 and an interface structure 111, and a plurality of light condensers 120, the plurality of waveguides 130, a plurality of electrodes 140, a plurality of electric connectors 150, and a modulator 160 may be installed on the interface structure 111. The interface structure 111 may be configured to be connected to the target. According to another example embodiment that is different from the illustrated example embodiment, the modulator 160 may not be installed on the interface structure 111 and be installed in a suitable location on an optical path between the power source 110 and the interface structure 111.

The power source 110 may include a light source configured to generate an optical signal. For example, the light source may include a light-emitting diode (LED). In this example, the light source may generate an optical signal with an actual single wavelength. In another example, the light source may generate an optical signal with multiple wavelengths. In addition, the power supply 110 in an integrated form may include a driving circuit to drive the light source, a battery to generate power, and a communication circuit to exchange communication signals externally, and the optical probe 10 may be provided in a wireless system.

The power source 110 and the interface structure 111 may be coupled to be detachable to each other. For example, the power source 110 may be a reusable part, and the interface structure 111 may be a disposable part.

The plurality of light condensers 120 may be configured to condense the optical signal. For example, the plurality of light condensers 120 may include a first lens 121 and a second lens 122. The first lens 121 may condense the optical signal of the light source in one direction, and the second lens 122 may condense the optical signal condensed from the first lens 121 in a direction intersecting with a direction in which the first lens 121 condenses the optical signal. In another example, the plurality of light condensers 120 may include only one of the first lens 121 and the second lens 122.

The plurality of light condensers 120 may not directly receive the optical signal generated from the light source. Only a selected light condenser 120 among the plurality of light condensers 120 may condense the optical signal transmitted through the modulator 160, and remaining light condensers 120 that are not selected may not receive the optical signal. The selected light condenser 120 may be also referred to as a target light condenser 120. The optical signal condensed by the plurality of light condensers 120 may be transmitted to the plurality of waveguides 130 corresponding to each of the plurality of light condensers 120. The plurality of light condensers 120 may be in a shape that is substantially disk-like and condense the optical signal in a plane direction.

The plurality of waveguides 130 may transmit the optical signal condensed from the plurality of light condensers 120 to the target. The plurality of waveguides 130 may be disposed to correspond to the plurality of light condensers 120. For example, the plurality of waveguides 130 may include a first end directly connected to one part of each of the plurality of light condensers 120, a second end that is close to the target object, and an extension portion that extends between the first end and the second end. In addition, the plurality of waveguides 130 and the plurality of light condensers 120 may be disposed on the same plane. By installing the plurality of light condensers 120 on the first end of the plurality of waveguides 130 in a direction facing the power source 110 on which the light source is installed, light transmission efficiency may be improved.

According to another example embodiment, the plurality of light condensers 120 may not be included in the optical probe 10. In such a case, the optical signal of the light source may be transmitted to the at least one waveguide 130 that is a target among the plurality of waveguides 130 by the modulator 160.

When the target is stimulated or suppressed by the optical signal that is transmitted to the target, the plurality of electrodes 140 may be configured to record the electrical signal generated by the target. The plurality of electrodes 140 may include a material having a low impedance. For example, the plurality of electrodes 140 may include iridium, carbon nanotubes, and the like. The plurality of electrodes 140 may be installed to a part adjacent to the second end of the plurality of waveguides 130.

The plurality of electric connectors 150 may be electrically connected to the plurality of electrodes 140 to receive the electrical signals from the plurality of electrodes 140 and transmit the electrical signals to the communication circuit of the power source 110.

The modulator 160 may transmit the optical signal generated from the power source 110 to at least one target light condenser 120 among the plurality of light condensers 120. The modulator 160 may be disposed between the power source 110 and the plurality of light condensers 120. The modulator 160 may select the target light condenser 120 from among the plurality of light condensers 120 and transmit the optical signal only to the target light condenser 120. As such, the modulator 160 may be different from a passive optical system (e.g., a condenser lens) that transmits the optical signal of the light source to all light condensers 120, and thus it is possible to selectively stimulate nerve cells at a predetermined position and extract the electrical signal generated thereby.

Although not illustrated herein, a plurality of interface structures 111 in which the plurality of light condensers 120, the plurality of waveguides 130, the plurality of electrodes 140, and the plurality of electric connectors 150 are installed may be formed in a multi-layer structure. When the optical probe 10 includes the plurality of light condensers 120, an optical path leading from the light source to the plurality of waveguides 130 through the plurality of light condensers 120 from the light source and an electrical path leading from the plurality of the electrodes 140 to the plurality of electric connectors 150 may be in a matrix form. That is, when the number of the interface structures 111 is N and the number of the plurality of light condensers 120 and the plurality of waveguides 130 is M, the optical path and the electrical path may be in an N×M matrix form. Hereinafter, example embodiments are described with respect to the optical probe 10 having an optical path and an electrical path in a 4×4 matrix form, but are not limited thereto. The optical probe 10 may be construed to have various paths shaped as a matrix and include a single interface structure (e.g., interface structure 111) in a matrix form including a 1×4 matrix form.

Figure 2:
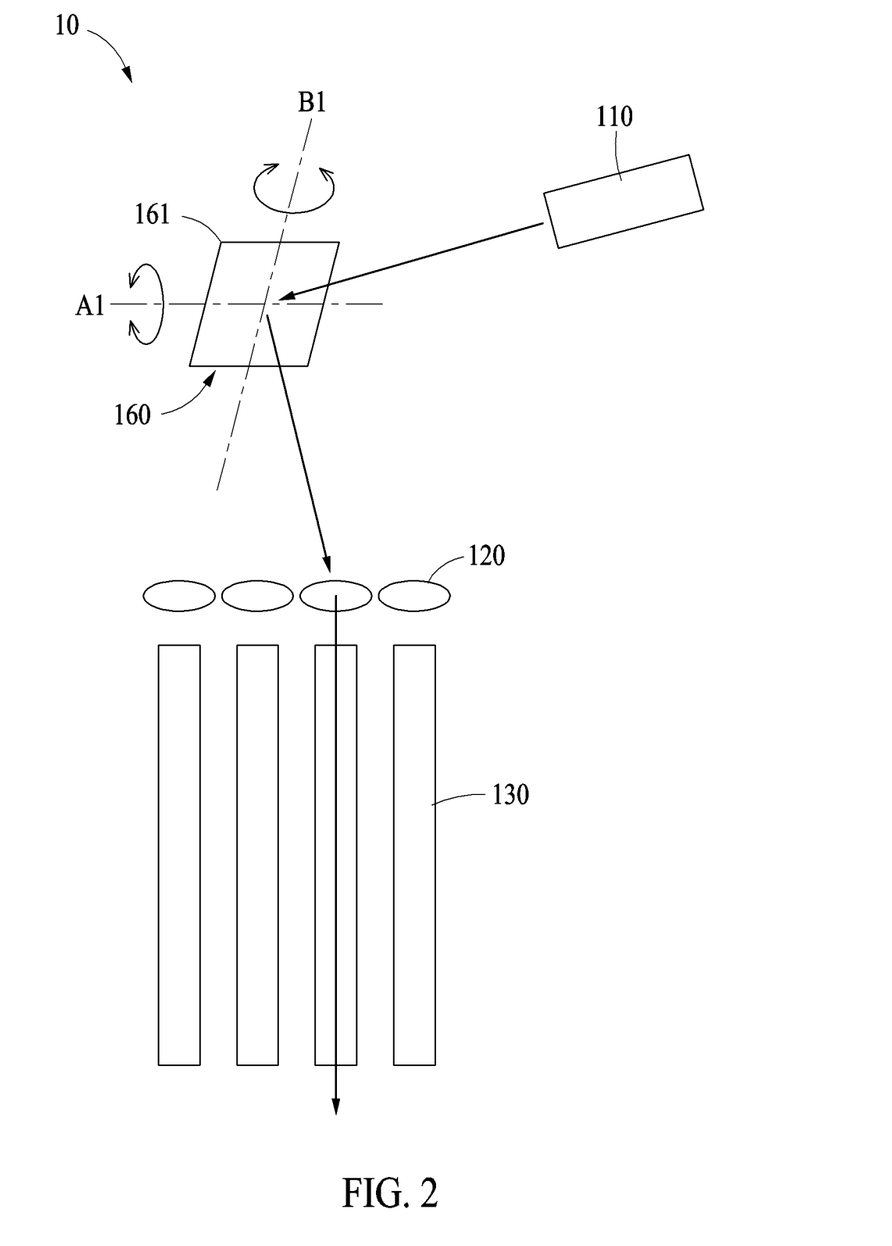
FIG. 2 is a diagram illustrating a modulator according to an example embodiment.

Referring to FIG. 2, the modulator 160 of the optical probe 10 described herein may include a mirror 161 that reflects an optical signal emitted from a light source of the power source 110 to one light condenser 120 of the plurality of light condensers 120 and/or one waveguide 130 of the plurality of waveguides 130. The mirror 161 may include a single reflective surface. The mirror 161 may be driven by a magnetic driving method or an electromagnetic driving method. For example, the modulator 160 may include a gimble to support the mirror 161, an elastically deformable spring to support the mirror 261 and the gimble, and a permanent magnet to drive the mirror 161 together with an electrical coil installed on the gimble.

Figure 3:
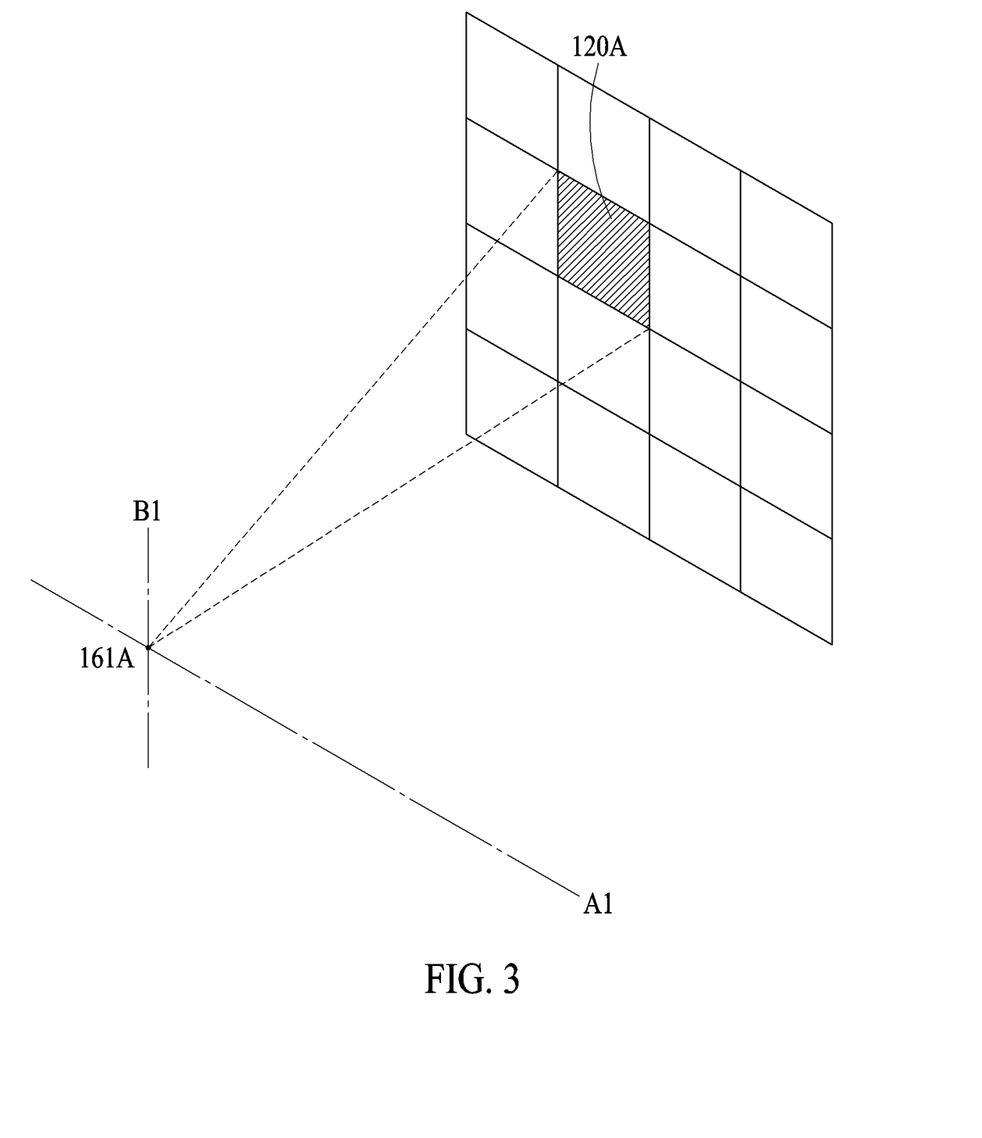
FIG. 3 is a diagram illustrating an optical signal transmission distribution being displayed by a modulator according to an example embodiment.

The mirror 161 may perform a two degree of freedom rotational movement that rotates around a first axis A1 of a first direction (i.e., a direction of a first axis) intersecting with a longitudinal direction of a waveguide 130 and a second axis B1 of a second direction (i.e., a direction of a second axis) intersecting with both the longitudinal direction of the waveguide 130 and the first direction of the first axis A1. In another example, the mirror 161 may perform a one degree of freedom rotational movement that rotates only around one of the first direction of the first axis A1 and the second direction of the second axis B1. For example, referring to FIG. 3, an optical signal reflected from an optical point 161A of the mirror 161 at which the first axis A1 and the second axis B1 meet may be transmitted to one area 120A among a plurality of areas of the plurality of light condensers 120 and the plurality of waveguides 130 in a matrix form. The optical signal may be transmitted to a target through one light condenser 120 and/or one waveguide 130 in the one area 120A. The one area 120A may be selected by rotating the first axis A1 and/or the second axis B1 of the mirror 161.

Figure 4:
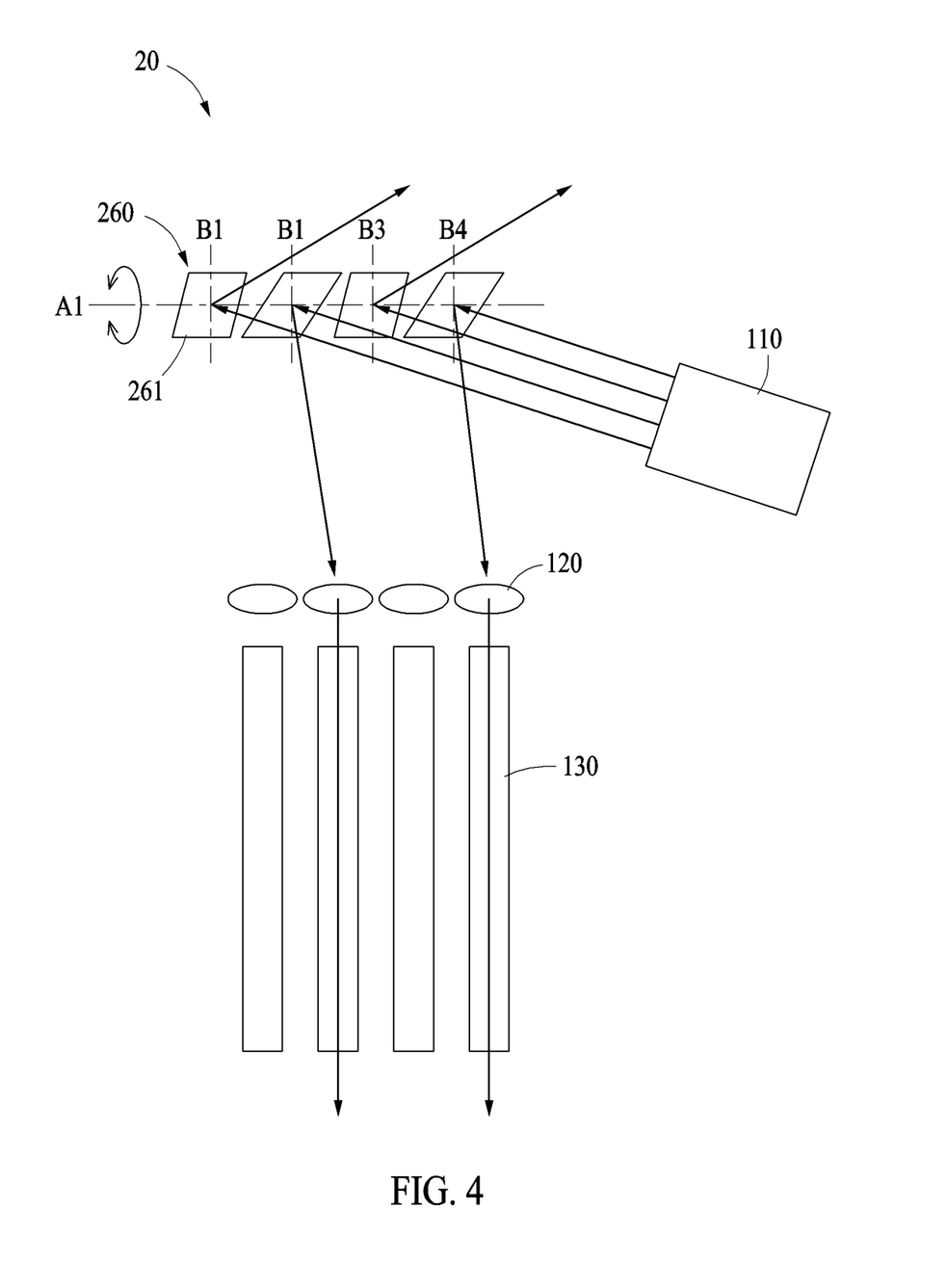
FIG. 4 is a diagram illustrating a modulator according to an example embodiment.
Figure 5:
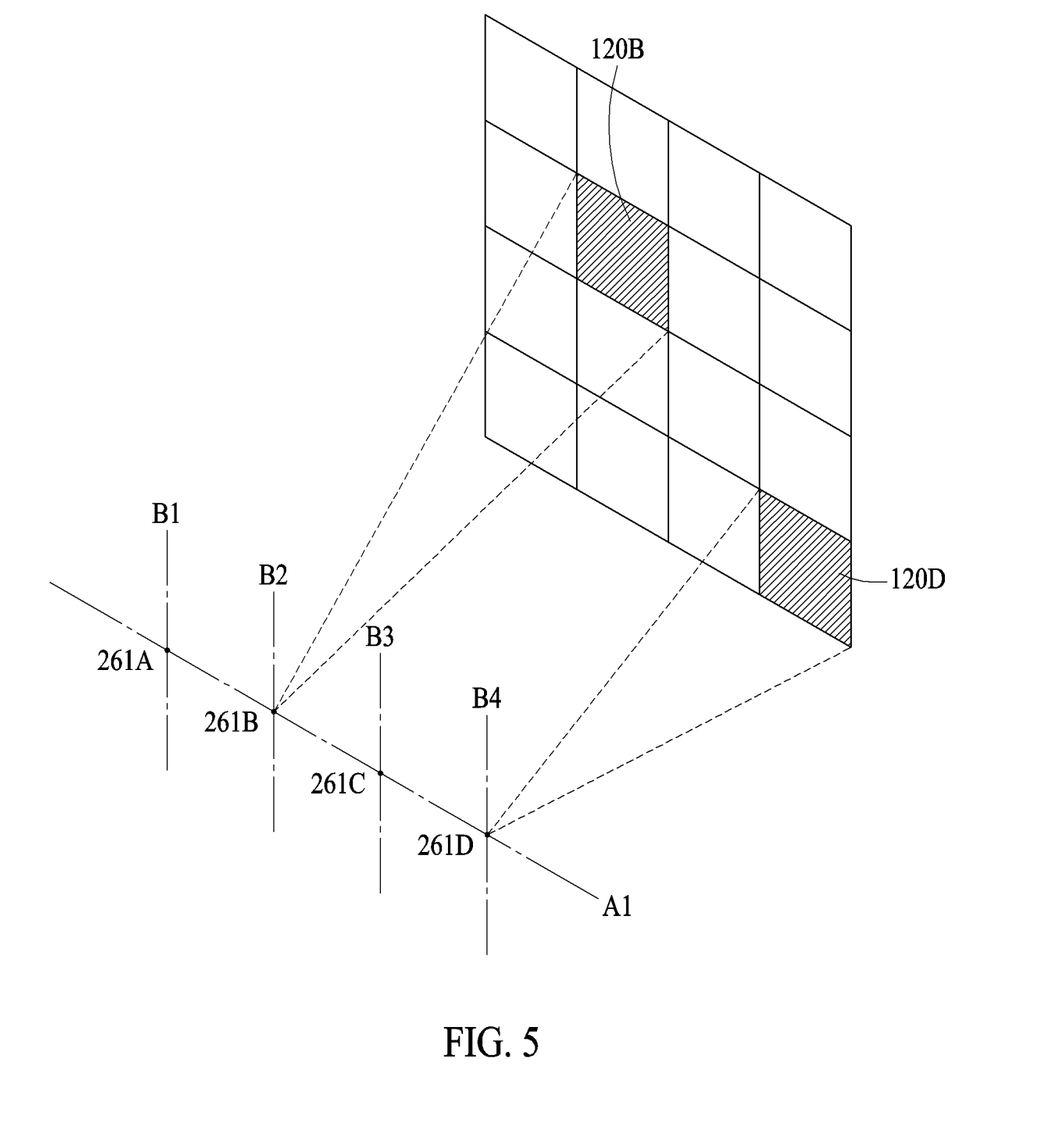
FIG. 5 is a diagram illustrating an optical signal transmission distribution being displayed by a modulator in FIG. 4 according to an example embodiment.

Referring to FIGS. 4 and 5, a modulator 260 of an optical probe 20 described herein may transmit an optical signal emitted from a light source of the power source 110 to parts of areas 120B and 120D forming a set pattern among a plurality of areas that are formed by the plurality of light condensers 120 and the plurality of waveguides 130 in a matrix form. In this example, the modulator 260 may include an array of mirrors 261. The number of the mirrors 261 may be the same as the number of the plurality of light condensers 120 or the number of the plurality of waveguides 130 included in each interface structure 111 with reference to FIG. 1.

Similar to the mirror 161 described with reference to FIG. 2, the mirrors 261 may be driven by a magnetic driving method or an electromagnetic driving method. The modulator 260 may include one or more gimbles to support each mirror 261, elastically deformable springs to support the mirrors 261 and the gimbles, and one or more permanent magnets to drive the mirrors 261 together with one or more electrical coils installed on the gimbles.

The mirrors 261 may perform a two degree of freedom rotational movement that rotates around a first axis A1 of a first direction intersecting with a longitudinal direction of the plurality of waveguides 130 and second axes B1, B2, B3, and B4 of a second direction intersecting with both the longitudinal direction of each waveguide 130 and the first direction of the first axis A1. In another example, the mirrors 261 may perform a one degree of freedom rotational movement that rotates only around one direction among the first axis A1 and each of the second axes B1, B2, B3, and B4. For example, an optical signal reflected from optical points 261B and 261D at which the first axis A1 and each of the second axes B1, B2, B3, and B4 meet may be transmitted to partial areas 120B and 120D among a plurality of areas of the plurality of light condensers 120 and the plurality of waveguides 130 in a matrix form. The optical signal may be transmitted to a target through one light condenser 120 and/or one waveguide 130 in the partial areas 120B and 120D. The partial areas 120B and 120D may be selected by rotating the mirrors 261 of the first axis A1 and/or the second axis B1. Two mirrors 261 of the mirrors 261 illustrated herein may reflect the optical signal to the partial areas 120B and 120D, while the remaining mirrors 261 not transmitting the optical signal to the partial areas 120B and 120D may reflect the optical signal outside of the optical probe 20.

The mirrors 261 may be driven in conjunction. The mirrors 261 being "driven in conjunction" may refer to the mirrors 261 performing a rotational movement around the first axis A1 for selecting the partial areas 120B and 120D forming at least one pattern that is predetermined based on a passage of time and/or around the second axes B1, B2, B3, and B4 of each of the plurality of mirrors 261. In such a case, a rotation of one mirror 261 may depend on a rotation of a different mirror 261.

The mirrors 261 may be driven independently. The mirrors 261 being "independently driven" refers to the mirrors 261 performing a rotational movement around the first axis A1 separately without the one mirror 261 being constrained by the different mirror 261 and/or around the second axes B1, B2, B3, and B4 of each mirror 261.

Figure 6:
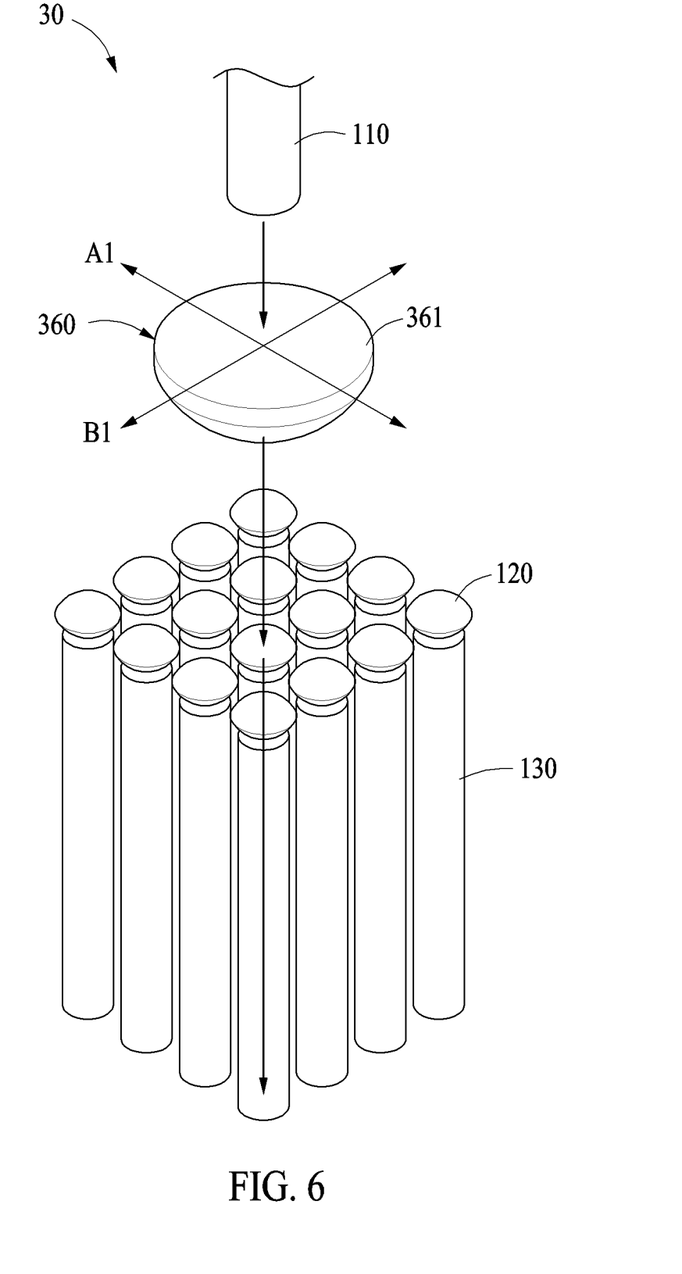
FIG. 6 is a diagram illustrating a modulator according to an example embodiment.

Referring to FIG. 6, a modulator 360 of an optical probe 30 described herein may include a movable light condenser element 361 for transmitting an optical signal emitted from a light source of the power source 110 to the plurality of light condensers 120 and/or the plurality of waveguides 130 corresponding to one row among the plurality of light condensers 120 and/or the plurality of waveguides 130 in a matrix form. In this example, the plurality of light condensers 120 may be referred to as a plurality of first light condensers 120, and the movable light condenser element 361 may be referred to as a second light condenser element 361 for classification. The second light condenser element 361 may be a convex lens.

The second light condenser element 361 may linearly move along the first axis A1 in a first direction intersecting with a longitudinal direction of the waveguide 130 and the second axis B1 in a second direction intersecting with both the longitudinal direction of the waveguide 130 and the first direction. Here, the first direction may be a direction parallel to a direction in which the plurality of waveguides 130 included in each interface structure are arranged.

Figure 7:
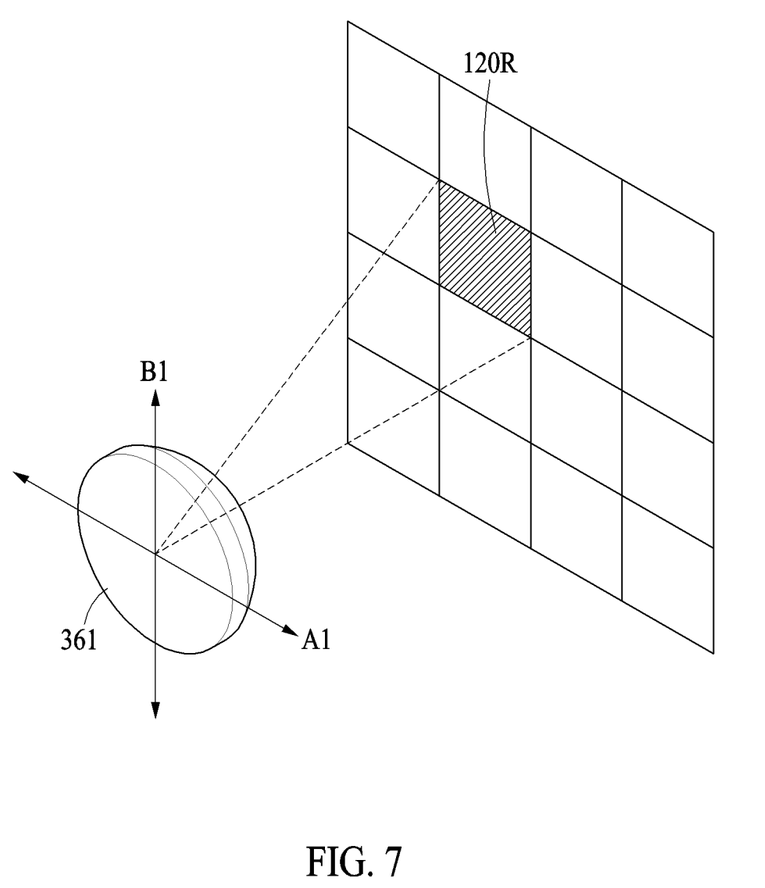
FIG. 7 is a diagram illustrating an optical signal transmission distribution being displayed by a modulator in FIG. 6 according to an example embodiment.

For example, referring to FIG. 7, when the second light condenser element 361 moves along the first axis A1 and the second axis B1 and stops at a set position, the optical signal of the light source may be transmitted to one area 120R among a plurality of areas in a matrix form. The transmitted optical signal may be transmitted to a target through a light condenser 120 and/or a waveguide 130 in the target one area 120R. An area to which the optical signal is transmitted among the matrix-shaped areas may be determined based on a result position following the linear movement of the second light condenser element 361.

Figure 8:
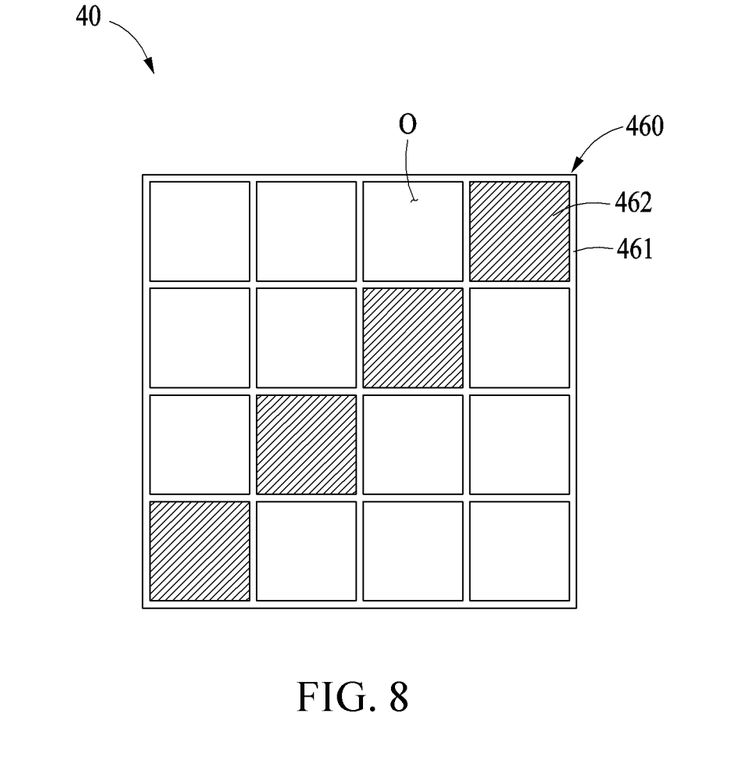
FIG. 8 is a diagram illustrating a modulator according to an additional example embodiment.

Referring to FIG. 8, a modulator 460 of an optical probe 40 described herein may use a method of partially blocking optical paths leading from a light source to a plurality of waveguides, opening remaining optical paths, and transmitting an optical signal through at least one waveguide among the plurality of waveguides.

For example, the modulator 460 may include a frame 461 having a plurality of openings O corresponding to the plurality of waveguides, respectively, and a plurality of opening degree control members 462 configured to open and close the plurality of openings O. The plurality of opening degree control members 462 may open only an opening O corresponding to the at least one target waveguide among the plurality of openings O and block the remaining openings O such that an optical path from the light source to the at least one target waveguide may be defined. The plurality of opening degree control members 462 may control an intensity of the optical signal through the at least one target waveguide by controlling a degree of opening (bending) of the plurality of openings.

Figure 9:
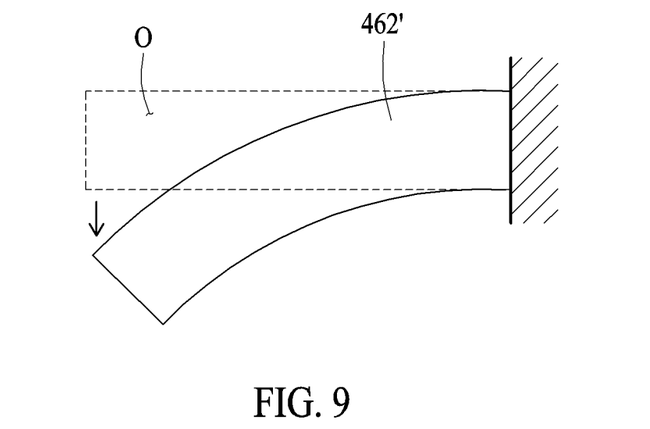
FIG. 9, is a diagram illustrating a cantilever arm for controlling a degree of opening of an opening in an optical path.

Referring to FIG. 9, the opening degree control member 462 in FIG. 8 may open and close an opening O and control a degree of bending of the opening O in a cantilever driving method. The opening degree control member 462 may include a cantilever arm 462'. Here, the modulator 460 may include a driving element (not shown) to control an inclination of the cantilever arm 462'. For example, the driving element may magnetically or electromagnetically attract the cantilever arm 462' to control a bending of the cantilever arm 462', and the opening may be controlled based on the degree of bending of the cantilever arm 462'.

Referring to FIG. 8, the opening degree control member 462 described herein may open an opening O using a liquid crystal. The opening degree control member 462 may include an organic compound having an optical anisotropy, and in such a case, the modulator 460 may further include a driving element (not shown) that determines a directionality of the organic compound. For example, the driving element may include a voltage application element to apply a voltage to the organic compound.

While this disclosure includes example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:
1. An optical probe, comprising:
   a light source configured to generate an optical signal;
   an interface structure having a proximal end and a distal end;
   a plurality of waveguides attached to the interface structure, each extending in a straight path from the proximal end to the distal end, each configured to guide the optical signal to a selected target and each having a first end for receiving the optical signal and a second end at the distal end configured to be close to the selected target;
   a plurality of electrodes configured to record an electrical signal generated by the selected target, wherein each of the plurality of electrodes is positioned on the second end of a corresponding respective one of each of the plurality of waveguides;
   a plurality of light condensers on the interface structure and connected to the plurality of waveguides for receiving the optical signal, wherein the first end of a corresponding one of each of the plurality of waveguides is directly connected to a respective one of each of the plurality of light condensers; and a modulator configured to transmit the optical signal of the light source to a selected target waveguide from among the plurality of waveguides.

2. The optical probe of claim 1, wherein the modulator comprises a single mirror that rotates around a first direction intersecting with a longitudinal direction of the plurality of waveguides and reflects the optical signal to the selected target waveguide.

3. The optical probe of claim 2, wherein the mirror rotates around a second direction intersecting with the longitudinal direction of the plurality of waveguides and the first direction.

4. The optical probe of claim 1, wherein the modulator comprises an array of mirrors disposed to correspond to the plurality of waveguides, wherein the mirrors rotate around a direction intersecting with a longitudinal direction of the plurality of waveguides and reflect the optical signal to the selected target waveguide.

5. The optical probe of claim 4, wherein the mirrors comprise:
 a first set comprising at least one mirror reflecting the optical signal in a direction toward the selected target waveguide; and
 a second set comprising remaining mirrors reflecting the optical signal in a direction not toward the plurality of waveguides.

6. The optical probe of claim 1, wherein the modulator comprises a light condensing element that linearly moves in a first direction intersecting with a longitudinal direction of the plurality of the waveguides or in a second direction intersecting with the longitudinal direction and the first direction for condensing the optical signal to the selected target waveguide.

7. The optical probe of claim 1, wherein the modulator comprises:
 a frame having a plurality of openings corresponding to the plurality of waveguides; and
 a plurality of opening degree control members configured to control an opening degree corresponding to the selected target waveguide among the plurality of openings.

8. The optical probe of claim 7, wherein the plurality of opening degree control members each comprises a cantilever arm, wherein the modulator further comprises a driving element configured to control a slope of the cantilever arm.

9. The optical probe of claim 7, wherein the plurality of opening degree control members each comprises an organic compound having an optical anisotropy, wherein the modulator further comprises a driving element configured to determine a directionality of the organic compound.

10. The optical probe of claim 1,
 wherein the plurality of light condensers include a first lens and a second lens, wherein the first lens is designed and configured to condense the optical signal in a first direction and the second lens is designed and configured to condense the optical signal condensed from the first lens in a second direction intersecting with the first direction.

* * * * *